United States Patent
Chen et al.

(10) Patent No.: US 11,187,642 B2
(45) Date of Patent: Nov. 30, 2021

(54) DEVICE AND PROCESS FOR MAINTAINING ZERO CAPILLARY PRESSURE BOUNDARY CONDITION DURING CORE FLOOD EXPERIMENTS

(71) Applicant: Saudi Arabian Oil Company, Dhahran (SA)

(72) Inventors: Quan Chen, Dhahran (SA); Sultan Enezi, Dhahran (SA); Ali Abdallah Al-Yousef, Dhahran (SA)

(73) Assignee: SAUDI ARABIAN OIL COMPANY

( * ) Notice: Subject to any disclaimer, the term of this patent is extended or adjusted under 35 U.S.C. 154(b) by 139 days.

(21) Appl. No.: 16/287,255

(22) Filed: Feb. 27, 2019

(65) Prior Publication Data

US 2020/0271563 A1     Aug. 27, 2020

(51) Int. Cl.
  *G01N 15/08* (2006.01)
  *G01N 33/24* (2006.01)
  *E21B 25/00* (2006.01)

(52) U.S. Cl.
  CPC ......... *G01N 15/0806* (2013.01); *G01N 33/24* (2013.01); *E21B 25/005* (2013.01)

(58) Field of Classification Search
  CPC ... G01N 15/0806; G01N 33/24; E21B 25/005
  See application file for complete search history.

(56) References Cited

U.S. PATENT DOCUMENTS

| | | |
|---|---|---|
| 2,618,151 A | 11/1952 | Leas |
| 3,018,660 A | 1/1962 | Schmid |
| 4,482,634 A | 11/1984 | Davis et al. |
| 4,669,299 A | 6/1987 | Closmann |
| 4,753,107 A | 6/1988 | Reed et al. |
| 4,868,751 A | 9/1989 | Dogru et al. |
| 5,164,672 A | 11/1992 | Gilliland et al. |
| 5,297,420 A | 3/1994 | Gilliland et al. |
| 5,311,766 A | 5/1994 | Persoff et al. |

(Continued)

OTHER PUBLICATIONS

Gupta et al., "Applications of the Intercept Method To Correct Steady State Relative Permeability for Capillary End-Effects", International Symposium of the Society of Core Analysts, 2015, pp. 1-12.

(Continued)

*Primary Examiner* — Ryan D Walsh
(74) *Attorney, Agent, or Firm* — Bracewell LLP; Constance Gall Rhebergen (57) ABSTRACT

A core sample holder assembly for performing core flood experiments includes a first end cap having a first cylindrical body with a first central chamber and a first inner end that is ring shaped, and a second end cap having a second cylindrical body with a second central chamber and a second inner end that is ring shaped. Three flow lines are spaced elevationally apart, the three flow lines extending from a first outward end to a first inward facing surface of each end cap. A flexible sleeve circumscribes the first end cap and the second end cap. A test sample bore is defined by the first inner end, the second inner end, and an inner diameter surface of the flexible sleeve. A central axis extends through the first end cap, the second end cap, and the flexible sleeve, the first end cap, the second end cap, and the flexible sleeve being axially aligned.

14 Claims, 3 Drawing Sheets

(56) References Cited

U.S. PATENT DOCUMENTS

| | | | |
|---|---|---|---|
| 5,341,101 A * | 8/1994 | Maerefat | G01N 15/08 324/376 |
| 5,363,692 A | 11/1994 | Lafargue et al. | |
| 5,493,226 A | 2/1996 | Honarpour et al. | |
| 5,563,333 A * | 10/1996 | Haines | G01N 15/0806 73/38 |
| 5,698,772 A | 12/1997 | Deruyter et al. | |
| 5,869,750 A * | 2/1999 | Onan | G01N 3/10 73/64.41 |
| 9,051,800 B2 | 6/2015 | Matthews et al. | |
| 9,903,826 B2 | 2/2018 | Alshehri et al. | |
| 2015/0219789 A1 * | 8/2015 | Pairoys | G01N 15/08 73/118.04 |
| 2017/0248506 A1 * | 8/2017 | Gupta | G01N 33/24 |
| 2018/0045704 A1 | 2/2018 | Al-Otaibi et al. | |
| 2020/0249182 A1 * | 8/2020 | Adebayo | G01N 24/081 |

OTHER PUBLICATIONS

International Search Report and Written Opinion for related PCT application PCT/US2020/020092 dated Jun. 24, 2020.

\* cited by examiner

DEVICE AND PROCESS FOR MAINTAINING ZERO CAPILLARY PRESSURE BOUNDARY CONDITION DURING CORE FLOOD EXPERIMENTS

BACKGROUND OF THE DISCLOSURE

1. Field of the Disclosure

The present disclosure relates to measuring properties of a subterranean formation, and more specifically, the disclosure relates to systems and methods for performing core flood testing on core samples from the subterranean formation.

2. Description of the Related Art

In hydrocarbon development operations, determining the characteristics of subterranean formations can be important, for example for determining strategies for improving or enhancing the recovery of hydrocarbons. Characteristics such as permeability, relative permeability, saturation change, capillary pressure, wettability and porosity can be measured.

Core flooding experiments can be performed on core samples taken from the subterranean formation. Core flooding experiments can be used, for example, to measure capillary pressure, wettability and relative permeability of the core sample.

SUMMARY OF THE DISCLOSURE

Systems and methods of this disclosure include a core sample holder that includes end caps with chambers that can contain a test or washing fluid. The chambers provide an axial distance between an inner face of the end cap and the core sample. The core sample holder in accordance with embodiments of this disclosure provide for the maintenance of a zero capillary pressure boundary condition which is required for capillary pressure (Pc) and relative permeability (Kr) measurements of core flood experiments using a steady-state equilibrium method. Embodiments of this disclosure can maintain an outlet boundary condition of zero capillary pressure, even at a high flow rate or high injection pressure. As used in this disclosure, a high flow rate is a flow rate greater than 40 milliliters per hour (ml/hour) and a high injection pressure is an injection pressure greater than the injection pressure corresponding to the flow rate of 40 ml/hour of injecting fluid.

In an embodiment of this disclosure a core sample holder assembly for performing core flood experiments includes a first end cap. The first end cap has a first cylindrical body having a first solid outer plug and a first hollow inner section. The first solid outer plug has a first outward end opposite the first hollow inner section. The first hollow inner section has an elongated ring shape with a first central chamber defining a first inward facing surface at an intersection of the first solid outer plug and the first hollow inner section. The first hollow inner section has a first inner end that is ring shaped and faces in a direction opposite the first outward end. The core sample holder assembly further includes three first flow lines spaced elevationally apart. The three first flow lines extend from the first outward end to the first inward facing surface.

The core sample holder assembly further includes a second end cap with a second cylindrical body. The second cylindrical body has a second solid outer plug and a second hollow inner section. The second solid outer plug has a second outward end opposite the second hollow inner section. The second hollow inner section has an elongated ring shape with a second central chamber defining a second inward facing surface at an intersection of the second solid outer plug and the second hollow inner section. The second hollow inner section has a second inner end that is ring shaped and faces in a direction opposite the second outward end. Three second flow lines are spaced elevationally apart, the three second flow lines extending from the second outward end to the second inward facing surface. A flexible sleeve circumscribing the first end cap and the second end cap. A test sample bore is defined by the first inner end, the second inner end, and an inner diameter surface of the flexible sleeve. A central axis extends through the first end cap, the second end cap, and the flexible sleeve, the first end cap, the second end cap, and the flexible sleeve being axially aligned.

In alternate embodiments the flexible sleeve can be formed of rubber. One or more of the three first flow lines can be an oil injection flow line, a second uppermost line of the three second flow lines can be a produced oil flow line, and a second lowermost line of the three second flow lines can be a washing injection fluid flow line. Alternately, one or more of the three second flow lines can be a brine injection flow line, a first uppermost line of the three first flow lines can be a washing injection fluid flow line, and a first lowermost line of the three first flow lines can be a produced brine fluid flow line. A first middle line of the three first flow lines can be a first different pressure testing line and a second middle line of the three second flow lines can be a second differential pressure testing line.

In other alternate embodiments, the first inward facing surface can be spaced axially apart from the first inner end by a distance equal to a first axial length of the first central chamber, and the second inward facing surface can be spaced axially apart from the second inner end by a distance equal to a second axial length of the second central chamber. The first axial length can be in a range of 0.5 millimeters (mm) to 5 mm and the second axial length is in a range of 0.5 mm to 5 mm.

In an alternate embodiment of this disclosure a core sample holder assembly for performing core flood experiments includes a first end cap having a first cylindrical body. The first cylindrical body has a first solid outer plug with a first outward end and an elongated ring shape with a first central chamber. The first central chamber has a first inner end that is ring shaped and faces in a direction opposite the first outward end. Three first flow lines are spaced elevationally apart, the three first flow lines extending through the first solid outer plug. A second end cap has a second cylindrical body. The second cylindrical body has a second solid outer plug with a second outward end and an elongated ring shape with a second central chamber. The second central chamber has a second inner end that is ring shaped and faces in a direction opposite the second outward end. Three second flow lines are spaced elevationally apart. The three second flow lines extend through the second solid outer plug. A flexible sleeve circumscribes the first end cap and the second end cap. A test sample bore is defined by the first end cap, the second end cap, and an inner diameter surface of the flexible sleeve. A central axis extends through the first end cap, the second end cap, and the flexible sleeve, the first end cap, the second end cap, and the flexible sleeve being axially aligned. A test fluid is located in at least one of the first central chamber and the second central chamber. A core sample is located within the test sample bore. The three first flow lines are spaced axially apart from a first end of the core sample by the first central chamber, and the three second flow lines are spaced axially apart from a second end of the core sample by the second central chamber.

In alternate embodiments one or more of the three first flow lines can be an oil injection flow line, a second uppermost line of the three second flow lines can be a produced oil flow line, and a second lowermost line of the three second flow lines can be a washing injection fluid flow line. Alternately, one or more of the three second flow lines can be a brine injection flow line, a first uppermost line of the three first flow lines can be a washing injection fluid flow line, and a first lowermost line of the three first flow lines can be a produced brine fluid flow line. A first middle line of the three first flow lines can be a first different pressure testing line and a second middle line of the three second flow lines can be a second differential pressure testing line. The first central chamber can have a first axial length in a range of 0.5 mm to 5 mm and the second central chamber can have a second axial length in a range of 0.5 mm to 5 mm.

In another alternate embodiment of this disclosure a method for performing core flood experiments with a core sample holder assembly includes locating a core sample within a test sample bore of the core sample holder assembly. The core sample holder assembly has a first end cap. The first end cap has a first cylindrical body having a first solid outer plug and a first hollow inner section. The first solid outer plug has a first outward end opposite the first hollow inner section. The first hollow inner section has an elongated ring shape with a first central chamber defining a first inward facing surface at an intersection of the first solid outer plug and the first hollow inner section. The first hollow inner section has a first inner end that is ring shaped and faces in a direction opposite the first outward end. Three first flow lines spaced elevationally apart, the three first flow lines extending from the first outward end to the first inward facing surface. A second end cap has a second cylindrical body. The second cylindrical body has a second solid outer plug and a second hollow inner section. The second solid outer plug has a second outward end opposite the second hollow inner section. The second hollow inner section has an elongated ring shape with a second central chamber defining a second inward facing surface at an intersection of the second solid outer plug and the second hollow inner section. The second hollow inner section has a second inner end that is ring shaped and faces in a direction opposite the second outward end. Three second flow lines are spaced elevationally apart, the three second flow lines extending from the second outward end to the second inward facing surface. A flexible sleeve circumscribes the first end cap and the second end cap. The test sample bore is defined by the first end cap, the second end cap, and an inner diameter surface of the flexible sleeve. A central axis extends through the first end cap, the second end cap, and the flexible sleeve, the first end cap, the second end cap, and the flexible sleeve being axially aligned. An injection fluid is delivered to an end of the core sample and an opposite end of the cores sample is washed with a washing fluid.

In alternate embodiments, delivering the injection fluid to the end of the core sample can include delivering an oil through one or more of the three first flow lines, and washing the opposite end of the core sample with the washing fluid can include delivering a brine through a second lowermost line of the three second flow lines and producing the oil through a second uppermost line of the three second flow lines. Alternately, delivering the injection fluid to the end of the core sample can include injecting a brine through one or more of the three second flow lines, and washing the opposite end of the core sample with the washing fluid can include injecting an oil through a first uppermost line of the three first flow lines, and producing the brine through a first lowermost line of the three first flow lines. The method can include measuring a first pressure differential through a first middle line of the three first flow lines and measuring a second pressure differential through a second middle line of the three second flow lines.

In other alternate embodiments, the first inward facing surface can be spaced axially apart from the first inner end by a distance equal to a first axial length of the first central chamber, and the second inward facing surface can be spaced axially apart from the second inner end by a distance equal to a second axial length of the second central chamber. The first axial length can be in a range of 0.5 mm to 5 mm and the second axial length is in a range of 0.5 mm to 5 mm.

BRIEF DESCRIPTION OF THE DRAWINGS

So that the manner in which the features, aspects and advantages of the embodiments of this disclosure, as well as others that will become apparent, are attained and can be understood in detail, a more particular description of the disclosure may be had by reference to the embodiments thereof that are illustrated in the drawings that form a part of this specification. It is to be noted, however, that the appended drawings illustrate only certain embodiments of the disclosure and are, therefore, not to be considered limiting of the disclosure's scope, for the disclosure may admit to other equally effective embodiments.

DETAILED DESCRIPTION

The disclosure refers to particular features, including process or method steps. Those of skill in the art understand that the disclosure is not limited to or by the description of embodiments given in the specification. The subject matter of this disclosure is not restricted except only in the spirit of the specification and appended Claims.

Those of skill in the art also understand that the terminology used for describing particular embodiments does not limit the scope or breadth of the embodiments of the disclosure. In interpreting the specification and appended Claims, all terms should be interpreted in the broadest possible manner consistent with the context of each term. All technical and scientific terms used in the specification and appended Claims have the same meaning as commonly understood by one of ordinary skill in the art to which this disclosure belongs unless defined otherwise.

As used in the Specification and appended Claims, the singular forms "a", "an", and "the" include plural references unless the context clearly indicates otherwise.

As used, the words "comprise," "has," "includes", and all other grammatical variations are each intended to have an open, non-limiting meaning that does not exclude additional elements, components or steps. Embodiments of the present disclosure may suitably "comprise", "consist" or "consist essentially of" the limiting features disclosed, and may be practiced in the absence of a limiting feature not disclosed. For example, it can be recognized by those skilled in the art that certain steps can be combined into a single step.

Where a range of values is provided in the Specification or in the appended Claims, it is understood that the interval encompasses each intervening value between the upper limit and the lower limit as well as the upper limit and the lower limit. The disclosure encompasses and bounds smaller ranges of the interval subject to any specific exclusion provided.

Where reference is made in the specification and appended Claims to a method comprising two or more defined steps, the defined steps can be carried out in any order or simultaneously except where the context excludes that possibility.

Figure 1:
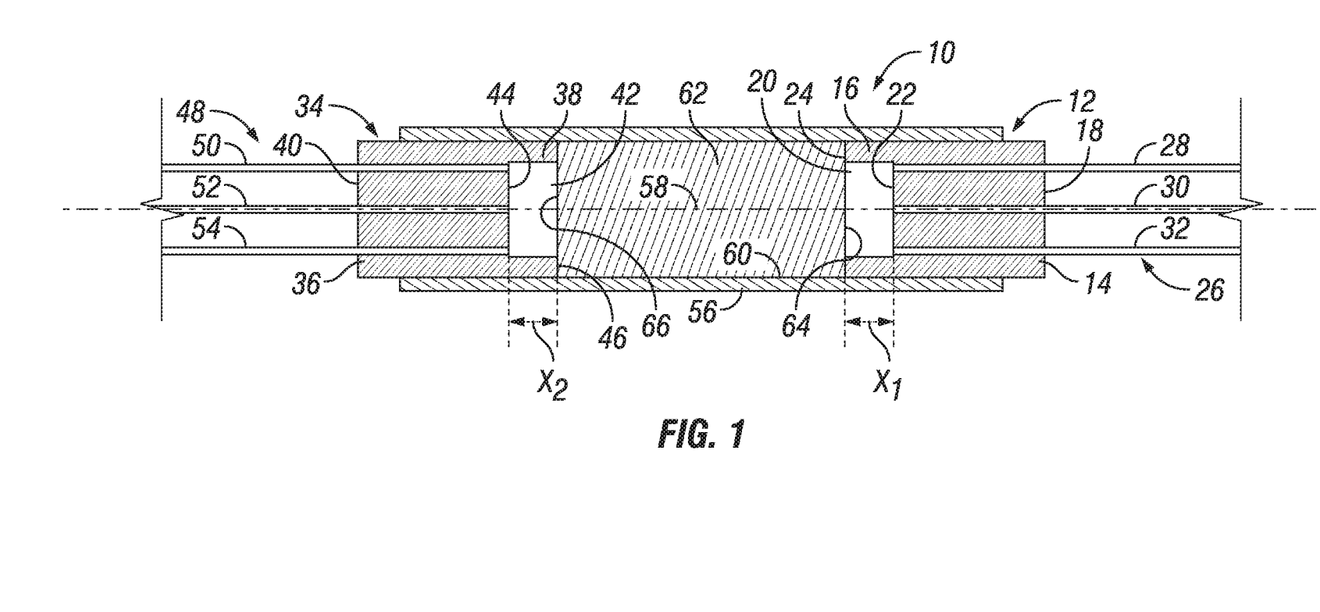
FIG. 1 is a section view of a core sample holder assembly in accordance with an embodiment of this disclosure.

Looking at FIG. 1, core sample holder assembly 10 can be used for performing core flood experiments. Core sample holder assembly 10 incudes first end cap 12. Looking at FIG. 2, first end cap 12 is a generally cylindrical shaped body made up of first solid outer plug 14 and first hollow inner section 16. First solid outer plug 14 is a solid cylindrical member with first outward end 18. First outward end 18 is a surface of first solid outer plug 14 that faces in a direction opposite first hollow inner section 16. First outward end 18 is an outermost end surface of first end cap 12.

Figure 2:
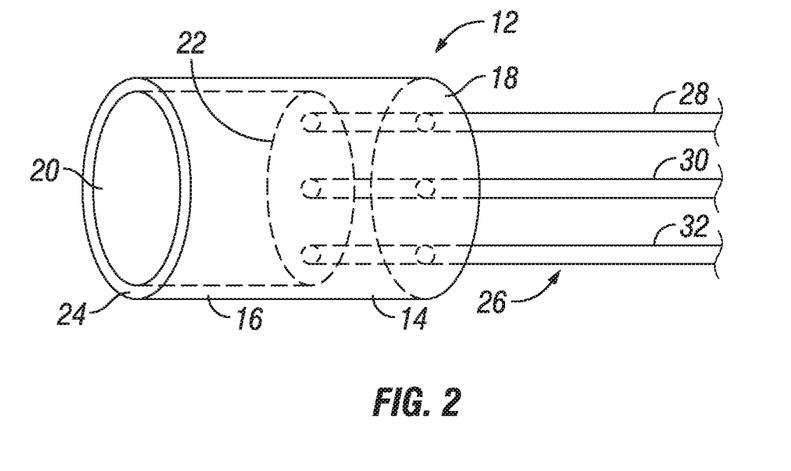
FIG. 2 is a perspective view of a first end of a core sample holder assembly in accordance with an embodiment of this disclosure.

First hollow inner section 16 is a tubular shaped member. First hollow inner section 16 has an elongated ring shape with an open central bore defining a first central chamber 20. Where first solid outer plug 14 meets first hollow inner section 16, first inward facing surface 22 is defined.

First inward facing surface 22 has a circular cross section and is a surface that faces in a direction opposite first outward end 18. First inward facing surface 22 is recessed relative to an inner most end of first end cap 12. First inward facing surface 22 has a diameter that is less than the outer diameter of first end cap 12. The inner most end of first end cap 12 is first inner end 24. First inner end 24 is ring shaped end surface and faces in a direction opposite first outward end 18. First inward facing surface 22 is spaced axially apart from first inner end 24 by a distance equal to a first axial length X1 of first central chamber 20. First axial length X1 can be in a range of 0.5 mm to 5 mm.

Three first flow lines 26 extend through first solid outer plug 14 from first outward end 18 to first inward facing surface 22. Three first flow lines 26 are spaced elevationally apart so that there is a first uppermost line 28, a first middle line 30, and a first lowermost line 32.

Looking at FIG. 1, core sample holder assembly 10 further incudes second end cap 34. Looking at FIG. 3, second end cap 34 can be similar or identical to first end cap 12, and when mounted as part of core sample holder assembly 10, first end cap 12 and second end cap 34 are oriented in opposite directions.

Figure 3:
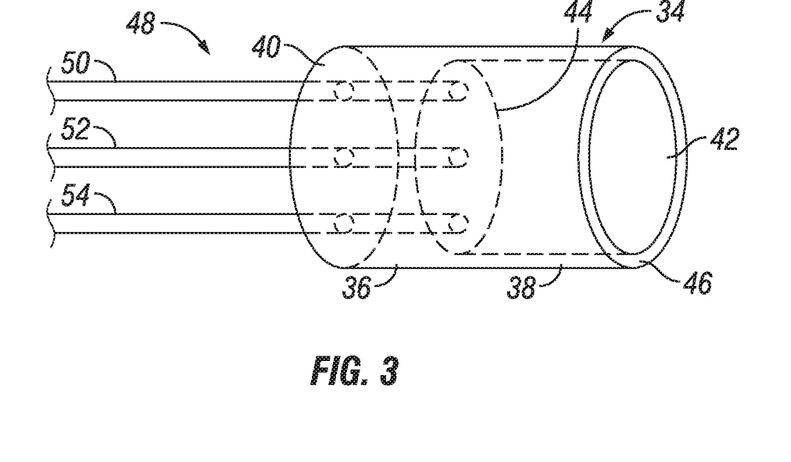
FIG. 3 is a perspective view of a second end of a core sample holder assembly in accordance with an embodiment of this disclosure.

Second end cap 34 is a generally cylindrical shaped body made up of second solid outer plug 36 and second hollow inner section 38. Second solid outer plug 36 is a solid cylindrical member with second outward end 40. Second outward end 40 is a surface of second solid outer plug 36 that faces in a direction opposite second hollow inner section 38. Second outward end 40 is an outermost end surface of second end cap 34.

Second hollow inner section 38 is a tubular shaped member. Second hollow inner section 38 has an elongated ring shape with an open central bore defining a second central chamber 42. Where second solid outer plug 36 meets second hollow inner section 38, second inward facing surface 44 is defined.

Second inward facing surface 44 has a circular cross section and is a surface that faces in a direction opposite second outward end 40. Second inward facing surface 44 is recessed relative to an inner most end of second end cap 34. Second inward facing surface 44 has a diameter that is less than the outer diameter of second end cap 34. The inner most end of second end cap 34 is second inner end 46. Second inner end 46 is ring shaped end surface and faces in a direction opposite second outward end 40. Second inward facing surface 44 is spaced axially apart from second inner end 46 by a distance equal to a second axial length X2 of second central chamber 42. Second axial length X2 can be in a range of 0.5 mm to 5 mm.

Three second flow lines 48 extend through second solid outer plug 36 from second outward end 40 to second inward facing surface 44. Three second flow lines 48 are spaced elevationally apart so that there is a second uppermost line 50, a second middle line 52, and a second lowermost line 54.

Some suitable materials for forming first end cap 12 and second end cap 34 include but are not limited to various stainless steels, alloys, and titanium for performing core flooding experiments at reservoir conditions. Such materials can withstand reservoir pressures and temperatures and have sufficient corrosion resistance to withstand reservoir high salinity brine, crude oil, and corrosive gas such as hydrogen sulfide ($H_2S$). In embodiments where an X-ray computerized tomography (CT) scanner is applied for the core flooding process for in-situ fluid saturation monitoring, x-ray transparent materials such as aluminum can be used for first end cap 12 and second end cap 34 and aluminum or carbon fiber composite materials can be used for the pressure vessel body. In embodiments where a magnetic resonance imaging (MM) scanner is applied to the core flooding process, MRI transparent materials such as polyether ether ketone (PEEK) can be used for first end cap 12 and second end cap 34 and glass fiber and PEEK composite materials can be used for the body of the pressure vessel.

Looking at FIG. 1, core sample holder assembly 10 further incudes flexible sleeve 56. Flexible sleeve 56 circumscribes at least a portion of first end cap 12 and second end cap 34. Flexible sleeve 56 can be formed, for example, of a fluoropolymer elastomer or a tetrafluoroethylene-propylene rubber and polytetrafluoroethylene (PTFE) heat shrink tube.

When flexible sleeve 56 circumscribes first end cap 12 and second end cap 34, central axis 58 extends through first end cap 12, second end cap 34, and flexible sleeve 56. First end cap 12, second end cap 34, and flexible sleeve 56 are axially aligned along central axis 58. Portions of first end cap 12 and second end cap 34 that are circumscribed by flexible sleeve 56 are co-axial with flexible sleeve 56.

Test sample bore 60 of core sample holder assembly 10 is defined by first inner end 24, second inner end 46, and an inner diameter surface of flexible sleeve 56. Core sample 62 is located within test sample bore 60. Core sample 62 can be a cylindrical sample that is removed from a subterranean formation.

When core sample 62 is mounted within test sample bore 60 of core sample holder assembly 10, first inner end 24 can contact core sample 62 around an outer edge of first end 64 of core sample 62. A central region of first end 64 is free of contact with first end cap 12. This central region of first end 64 is in fluid communication with first central chamber 20. When core sample 62 is mounted within test sample bore 60 of core sample holder assembly 10 three first flow lines 26 are spaced axially apart from first end 64 of core sample 62 by first central chamber 20. Therefore three first flow lines 26 are spaced axially apart from first end 64 of core sample 62 by first axial length X1 of first central chamber 20.

When core sample 62 is mounted within test sample bore 60 of core sample holder assembly 10, second inner end 46 can contact core sample 62 around an outer edge of second end 66 of core sample 62. A central region of second end 66 is free of contact with second end cap 34. This central region of second end 66 is in fluid communication with second central chamber 42. When core sample 62 is mounted within test sample bore 60 of core sample holder assembly 10 three second flow lines 48 are spaced axially apart from second end 66 of core sample 62 by second central chamber 42. Therefore three second flow lines 48 are spaced axially apart from second end 66 of core sample 62 by second axial length X2 of second central chamber 42.

In an example of operation, core sample 62 can be located within test sample bore 60 within flexible sleeve 56 and between first end cap 12 and second end cap 34. The core sample holder assembly 10 is placed and contained in a suitable pressure vessel (not shown in FIG. 1). The core sample assemble 10 can be hydrostatically pressurized by injecting confining fluid into the void between the pressure vessel and the core sample holder assembly 10. The hydrostatic pressure can be up to ten thousand pounds per square inch. Characteristics of core sample 62 can be measured by delivering an injection fluid to either first end 64 or second end 66 of core sample 62 and washing the other of the first end 64 or second end 66 of core sample 62 with a washing fluid.

As an example of a test procedure, a steady-state equilibrium between viscous force and capillary force may be achieved by injecting first fluid, such as oil, into one of the ends of core sample 62. In such a test core sample 62 can first be saturated with a second fluid, such as brine. Core sample 62 can be washed at the other end of core sample 62 with the second fluid. For example, if a fluid is injected into first end 64 of core sample 62, the second end 66 of core sample 62 is washed. Alternately, if a fluid is injected into second end 66 of core sample 62, the first end 64 of core sample 62 is washed.

In embodiments of this disclosure first central chamber 20 and second central chamber 42 are sized to that an outlet boundary condition of zero Pc may be achieved, even in test with a high flow rate or a high injection pressure, such as tests with a flow rate greater than 40 ml/hour.

During certain example tests, one or more of three first flow lines 26 is an oil injection flow line, second uppermost line 50 of three second flow lines 48 is a produced oil flow line, and second lowermost line 54 of three second flow lines 48 is a washing injection fluid flow line. In alternate example tests, one or more of three second flow lines 48 is a brine injection flow line, first uppermost line 28 of three first flow lines 26 is a washing injection fluid flow line, and first lowermost line 32 of three first flow lines 26 is a produced brine fluid flow line. During any of the test procedures, first middle line 30 can be a first differential pressure testing line and second middle line 52 can be a second differential pressure testing line. During any of the test procedures, amounts of a test fluid, such as injection fluid, washing fluid, or both injection fluid and test fluid can be located within first central chamber 20 or second central chamber 42.

Figure 4:
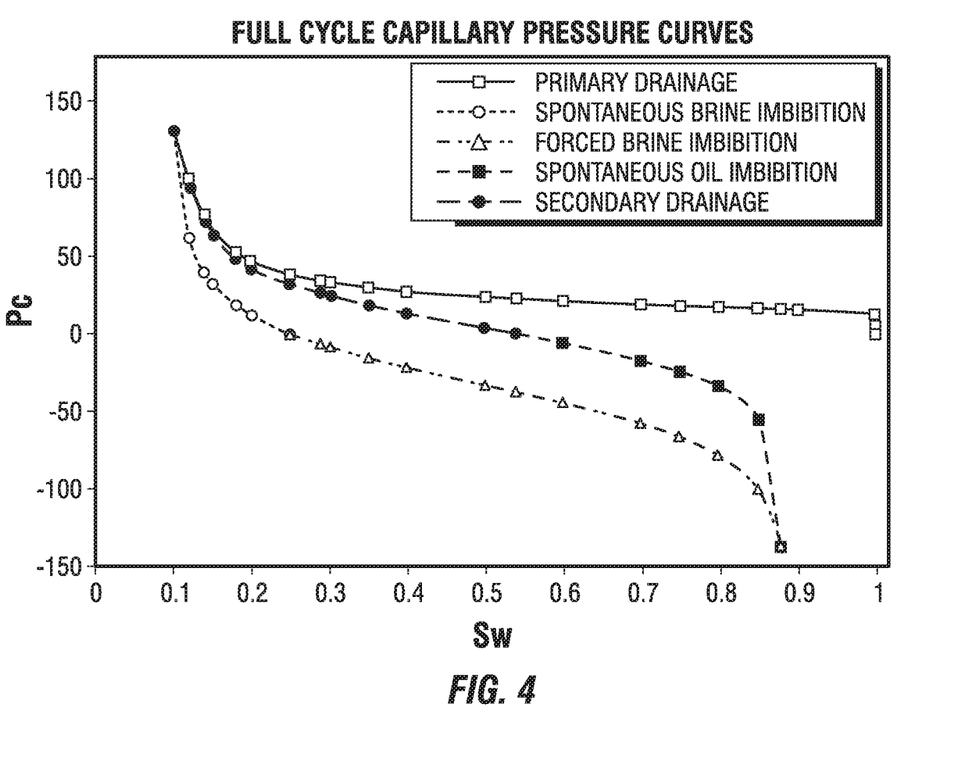
FIG. 4 shows full cycle capillary pressure curves illustrating test results derived from the use of a core sample holder, in accordance with an embodiment of this disclosure.

Looking at FIG. 4, a full cycle of capillary pressure curves is shown, which consist of primary drainage, spontaneous brine imbibition, forced brine imbibition, spontaneous oil imbibition, and secondary drainage curves. FIG. 4 plots capillary pressure (Pc) against water saturation (Sw). The unit for capillary pressure (Pc) is psi, and water saturation is dimensionless and has a range between 0 and 1.

In order to perform the primary drainage, spontaneous brine imbibition, and secondary drainage tests, oil was injected into core sample 62 through first end cap 12. Brine face washing resulted in produced oil from core sample 62 being washed away from second end 66 of core sample 62 and through second end cap 34. During the face washing process, the brine washing fluid, which is heavier than the oil, was injected into second central chamber 42 by way of second lowermost line 54. Produced oil exited second central chamber 42 through second uppermost line 50.

In order to perform the forced brine imbibition and spontaneous oil imbibition tests brine was injected into core sample 62 through second end cap 34. Oil face washing resulted in produced brine from core sample 62 being washed away from first end 64 of core sample 62 and through first end cap 12. During the oil face washing process, the oil washing fluid, which was lighter than the brine, was injected into first central chamber 20 by way of first uppermost line 28. Produced brine exited first central chamber 20 through first lowermost line 32.

During any of the face washing process the heavier fluid passes through the applicable lowermost line 32 or 54 and the lighter fluid passes through the applicable uppermost line 28 or 50, regardless of which fluid is being injected and which fluid is being produced. Having an uppermost line and a lowermost line and using the heavier washing fluid bottom-up and lighter washing fluid top-down enables gravity to maintain the washing fluid reservoir level and to wash away produced fluid effectively.

In order to obtain the desired Pc value of zero at the end of spontaneous brine imbibition and at the end of spontaneous oil imbibition, the faces of both first end 64 and second end 66 of core sample 62 require simultaneously face washing by oil and brine, respectively. The test procedures for both oil face washing and brine face washing to be carried out simultaneously can include: (1) passing oil through uppermost line 28 into the first central chamber 20 of the first end cap 12 and through the first end 64 of core sample 62 and through lowermost line 32 out of the first central chamber 20; (2) passing brine through lowermost line 54 into the second central chamber 42 of the second end cap 34 and through the second end 66 of core sample 62 and through the uppermost line 50 out of the second central chamber 42.

Embodiments described in this disclosure therefore provide systems and methods that include a chamber that maintains a small reservoir of washing fluid at outlet and a small reservoir of injecting fluid at inlet. The fluid in the chambers contact the faces of the core sample. In such embodiments washing fluid does not disturb fluid flow inside the rock core sample. The embodiments further maintain continuity between washing fluid in the chamber and inside of the core sample, and allow for an outlet boundary condition of zero capillary pressure. The outlet boundary condition of zero capillary pressure is important, because such a condition allows for the capillary pressure to be determined by the differential pressure between the inlet and the outlet when a steady state equilibrium is reached.

Systems and methods of this disclosure enable an uninterrupted spontaneous imbibition of washing fluid from the chamber into the core sample when the pressure of the injected fluid decreases. A zero Pc can be maintained at every location of the core sample during data acquisition of zero Pc value at the end of the spontaneous brine imbibition test and at the end of the spontaneous oil imbibition test. Current embodiments further prevent rock material from blocking the flow distribution grooves on the inlet and outlet end platens of currently available end-pieces. The chamber of the end caps of embodiments of this disclosure maintains a small reservoir of washing fluid at the outlet and a small reservoir of injecting fluid at the inlet, and the fluid in the reservoir contacts the rock core faces. There are several technical advantages of embodiments of this disclosure, including:

the washing fluid does not disturb fluid flow inside the rock core sample;

a continuity between washing fluid in the chamber and inside of the core sample, and outlet boundary condition of zero capillary pressure can be maintained;

an uninterrupted spontaneous imbibition of washing fluid from the chamber into the core sample is enabled when the pressure of the injected fluid decreases;

a zero Pc can be maintained at every location of the core sample during data acquisition of zero Pc value at the end of the spontaneous brine imbibition test and at the end of the spontaneous oil imbibition test; and rock material is prevented from blocking the flow distribution grooves on the inlet and the outlet end plates of the common end-pieces reducing the risk that a severe blockage ruins a core flood test.

Furthermore, the present design of one flow line at bottom and other flow line at the top of the end caps, and the washing fluid injection configuration i.e., heavier fluid bottom-up and lighter fluid top-down, enables the gravity to maintain the washing fluid reservoir level and to wash away produced fluid effectively.

The current systems which cannot maintain required zero Pc boundary condition lead to considerable error in the relevant test results.

Because embodiments of this disclosure provide full cycle relative permeability and capillary pressure curves that can be measured with single core sample and one set of tests, the amount of time, core samples, and manpower spent to conduct separate relative permeability and capillary pressure tests is reduced compared to currently available techniques.

Embodiments of this disclosure, therefore, are well adapted to carry out the objects and attain the ends and advantages mentioned, as well as others that are inherent. While embodiments of the disclosure has been given for purposes of disclosure, numerous changes exist in the details of procedures for accomplishing the desired results. These and other similar modifications will readily suggest themselves to those skilled in the art, and are intended to be encompassed within the spirit of the present disclosure and the scope of the appended claims.

What is claimed is:

1. A core sample holder assembly for performing core flood experiments, the core sample holder assembly including:
    a first end cap having;
        a first cylindrical body having a first solid outer plug and a first hollow inner section, the first solid outer plug having a first outward end opposite the first hollow inner section, and the first hollow inner section having an elongated ring shape with a first central chamber defining a first inward facing surface at an intersection of the first solid outer plug and the first hollow inner section, the first hollow inner section having a first inner end that is ring shaped and faces in a direction opposite the first outward end; and
        three first flow lines spaced elevationally apart, the three first flow lines extending from the first outward end to the first inward facing surface;
    a second end cap having;
        a second cylindrical body having a second solid outer plug and a second hollow inner section, the second solid outer plug having a second outward end opposite the second hollow inner section, and the second hollow inner section having an elongated ring shape with a second central chamber defining a second inward facing surface at an intersection of the second solid outer plug and the second hollow inner section, the second hollow inner section having a second inner end that is ring shaped and faces in a direction opposite the second outward end; and
        three second flow lines spaced elevationally apart, the three second flow lines extending from the second outward end to the second inward facing surface;
    a flexible sleeve circumscribing the first end cap and the second end cap;
    a test sample bore, the test sample bore defined by the first inner end, the second inner end, and an inner diameter surface of the flexible sleeve; and
    a central axis extending through the first end cap, the second end cap, and the flexible sleeve, the first end cap, the second end cap, and the flexible sleeve being axially aligned; where
    one or more of the three first flow lines is an oil injection flow line, a second uppermost line of the three second flow lines is a produced oil flow line, and a second lowermost line of the three second flow lines is a washing fluid injection flow line.

2. The core sample holder assembly of claim 1, where the flexible sleeve is formed of rubber.

3. The core sample holder assembly of claim 1, where a first middle line of the three first flow lines is a first differential pressure testing line and a second middle line of the three second flow lines is second differential pressure testing line.

4. The core sample holder assembly of claim 1, where the first inward facing surface is spaced axially apart from the first inner end by a distance equal to a first axial length of the first central chamber, and the second inward facing surface is spaced axially apart from the second inner end by a distance equal to a second axial length of the second central chamber.

5. The core sample holder assembly of claim 4, where the first axial length is in a range of 0.5 mm to 5 mm and the second axial length is in a range of 0.5 mm to 5 mm.

6. A core sample holder assembly for performing core flood experiments, the core sample holder assembly including:
    a first end cap having;
        a first cylindrical body having a first solid outer plug with a first outward end and an elongated ring shape with a first central chamber, the first central chamber having a first inner end that is ring shaped and faces in a direction opposite the first outward end; and
        three first flow lines spaced elevationally apart, the three first flow lines extending through the first solid outer plug;
    a second end cap having;
        a second cylindrical body having a second solid outer plug with a second outward end and an elongated ring shape with a second central chamber, the second central chamber having a second inner end that is ring shaped and faces in a direction opposite the second outward end; and three second flow lines spaced elevationally apart, the three second flow lines extending through the second solid outer plug;

a flexible sleeve circumscribing the first end cap and the second end cap;

a test sample bore, the test sample bore defined by the first end cap, the second end cap, and an inner diameter surface of the flexible sleeve;

a central axis extending through the first end cap, the second end cap, and the flexible sleeve, the first end cap, the second end cap, and the flexible sleeve being axially aligned;

a test fluid located in at least one of the first central chamber and the second central chamber; and a core sample located within the test sample bore, where the three first flow lines are spaced axially apart from a first end of the core sample by the first central chamber, and the three second flow lines are spaced axially apart from a second end of the core sample by the second central chamber; where one or more of the three second flow lines is a brine injection flow line, a first uppermost line of the three first flow lines is a washing fluid injection flow line, and a first lowermost line of the three first flow lines is a produced brine flow line.

7. The core sample holder assembly of claim 6, where a first middle line of the three first flow lines is a first differential pressure testing line and a second middle line of the three second flow lines is second differential pressure testing line.

8. The core sample holder assembly of claim 6, where the first central chamber has a first axial length in a range of 0.5 mm to 5 mm and the second central chamber has a second axial length in a range of 0.5 mm to 5 mm.

9. A method for performing core flood experiments with a core sample holder assembly, the method including:

locating a core sample within a test sample bore of the core sample holder assembly, the core sample holder assembly having:

a first end cap having;

a first cylindrical body having a first solid outer plug and a first hollow inner section, the first solid outer plug having a first outward end opposite the first hollow inner section, and the first hollow inner section having an elongated ring shape with a first central chamber defining a first inward facing surface at an intersection of the first solid outer plug and the first hollow inner section, the first hollow inner section having a first inner end that is ring shaped and faces in a direction opposite the first outward end; and three first flow lines spaced elevationally apart, the three first flow lines extending from the first outward end to the first inward facing surface;

a second end cap having;

a second cylindrical body having a second solid outer plug and a second hollow inner section, the second solid outer plug having a second outward end opposite the second hollow inner section, and the second hollow inner section having an elongated ring shape with a second central chamber defining a second inward facing surface at an intersection of the second solid outer plug and the second hollow inner section, the second hollow inner section having a second inner end that is ring shaped and faces in a direction opposite the second outward end; and three second flow lines spaced elevationally apart, the three second flow lines extending from the second outward end to the second inward facing surface;

a flexible sleeve circumscribing the first end cap and the second end cap;

the test sample bore defined by the first end cap, the second end cap, and an inner diameter surface of the flexible sleeve; and a central axis extending through the first end cap, the second end cap, and the flexible sleeve, the first end cap, the second end cap, and the flexible sleeve being axially aligned; and delivering an injection fluid to an end of the core sample and washing an opposite end of the core sample with a washing fluid.

10. The method of claim 9, where delivering the injection fluid to the end of the core sample includes delivering an oil through one or more of the three first flow lines, and washing the opposite end of the core sample with the washing fluid includes delivering a brine through a second lowermost line of the three second flow lines and producing the oil through a second uppermost line of the three second flow lines.

11. The method of claim 9, where delivering the injection fluid to the end of the core sample includes injecting a brine through one or more of the three second flow lines, and washing the opposite end of the core sample with the washing fluid includes injecting an oil through a first uppermost line of the three first flow lines, and producing the brine through a first lowermost line of the three first flow lines.

12. The method of claim 9, further including measuring a first pressure differential through a first middle line of the three first flow lines and measuring a second pressure differential through a second middle line of the three second flow lines.

13. The method of claim 9, where the first inward facing surface is spaced axially apart from the first inner end by a distance equal to a first axial length of the first central chamber, and the second inward facing surface is spaced axially apart from the second inner end by a distance equal to a second axial length of the second central chamber.

14. The method of claim 13, where the first axial length is in a range of 0.5 mm to 5 mm and the second axial length is in a range of 0.5 mm to 5 mm.

* * * * *